United States Patent [19]

van Leeuwen

[11] Patent Number: Plant 6,381

[45] Date of Patent: Nov. 8, 1988

[54] ALSTROEMERIA NAMED ADVENDO

[75] Inventor: Jac. van Leeuwen, Poeldijk, Netherlands

[73] Assignee: Lezan V.O.F., Hillegom, Netherlands

[21] Appl. No.: 2,551

[22] Filed: Jan. 12, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler

[57] ABSTRACT

A new and distinct variety of alstroemeria of the butterfly type particularly distinguished by its continuous year-around and profuse production of medium large flowers distinguished by the reddish violet coloration of its relatively large outer petals, and at the base and tips of its heavily striped inner petals, the flowers being borne singly on short, rigid peduncles comprising an umbel formation carried on a strong, relatively tall cane, the flowers having a very good lasting quality both on the plant and as cut flowers.

1 Drawing Sheet

BACKGROUND OF THE NEW PLANT

This new alstroemeria hybrid originated as a seedling of unknown parentage discovered by me in greenhouse at Hillegom, The Netherlands, in 1978, growing among a group of seedlings of various alstroemeria plants maintained for breeding purposes. Because of the very unusual coloration of its flowers this particular seedling was selected by me for propagaton, which was done by me by rhizome division with such satisfactory results that this type of propagation was carried on under my direction through several successive generations, which demonstrated conclusively that the noval and distinctive characteristics of the discovery plant were fully present in the clones from generation to generation and appeared to be firmly fixed. Present propagation of this new alstroemeria cultivar is being carried on at Hillegom and at Aalsmeer in The Netherlands.

DESCRIPTION OF THE DRAWING

This alstroemeria cultivar is illustrated by the accompanying photographic drawing, which in the left hand view shows a pair of flowering stems to illustrate the umbel arrangement of the inflorescence; and the right hand view is a close-up of a typical umbel showing the arrangement of the inflorescence in more detail, the color rendition being as nearly true as it is reasonably possible to obtain by conventional photographic procedures.

DESCRIPTION OF THE NEW PLANT

The following is a detailed description of my new butterfly type alstroemeria plant with the color designations being according to The R.H.S. Colour Chart published by The Royal Horticultural Society of London, England.

THE PLANT

Origin: Seedling.
Parentage: Unknown.
Classification:
- *Botanic.*—Alstroemeria Hybrid (Butterfly Type).
- *Commercial.*—Butterfly Alstroemeria.

Form: Bush, as a perennial plant.
Shape: Normal.
Height: From 100 to about 120 cm.

Main stem or cane length: Averaging about 150 cm.
Branching character: Numerous stems from one plant.
Growth: Very strong and upright.
Foliage:
- *Quantity.*—Average.
- *Number of leaves.*—One pair to each internodium.
- *Leaf size.*—About 8.8 cm. long.
- *Leaf shape.*—Oval with entire margins.
- *Texture.*—Leathery.
- *Color.*—Upper side — Dark green. Under side — Medium green.

Rhizomes:
- *Size.*—About 9 inches long, depending on season.
- *Color.*—Pale white.

THE BUD

Form: Ovoid, sometimes elliptic.
Size:
- *Length.*—About 2.8 cm.
- *Diameter.*—About 1.4 cm.

Opening Rate: Normal.
Sepals:
- *Number.*—Six.
- *Shape.*—Cuneate and when the flowers open, the sepals curl back.

Peduncle:
- *Length.*—Averaging about 7.5 cm.
- *Character.*—Rigid.
- *Color.*—Medium green.

THE FLOWER

Blooming habit: Continuously and profusely.
Size: Medium large.
Borne: On relatively short peduncles comprising an umbel cluster.
Shape:
- *When bloom first opens.*—Cup-shaped.
- *As bloom matures.*—The form becomes more flat.

Petalage:
- *Number of petals.*—Six.
- *Shape.*—Cuneate, with somewhat ruffled margins and a rather flat, emarginate apex.
- *Texture.*—Leathery.
- *Appearance.*—Shiny.
- *Color.*—Outer Petals: Mainly reddish violet, 68A-B, with a very large and darker central blotch, RHS 64A-B. Reverse Side: Mainly RHS 68B with a large and darker central blotch of RHS 59B-C. Inside Petals: Reddish violet, 68A-B, at the tip with a yellow blotch, 3B, at the center below a creamy white area immediately below the reddish tip. The inner petals have many dark violet red stripes extending longitudinally from base to tip. Reverse Side: The same as the top side but without stripes.

Peduncle:

*Length.*—About 7.5 cm.

*Strength.*—Strong and upright.

*Color.*—Medium green with anthocyane shading.

Discoloration after full bloom: The color becomes more purple.

Disease resistance: Resistance to *Fusarium oxysporum* as observed in The Netherlands.

Lasting quality: Very good both on the plant and as a cut flower.

REPRODUCTIVE ORGANS

Stamens:

*Number.*—Six.

*Arrangement.*—Around the pistil.

*Anthers.*—Size: About 1.3 cm. Color: Olive green.

*Filaments.*—Length: About 1.3 cm. Color: Light purple.

*Pollen.*—Color: Light purple.

*Pistils.*—Number: One.

*Style.*—Length: About 3.8 cm. Color: Light purple.

*Stigmas.*—Color. Light purple shaded with light salmon.

Character of ovaries: Light to medium green in color with an anthocyane shade which can be medium to strong on and between the ribs.

FRUIT

Fertility: The fruit is fertile.

Shape: Ovoid.

Color at maturity: Green.

This new alstroemeria variety most nearly resembles the variety 'Rosario' (unpatented) with respect to type of bloom and, in color, the variety 'Lilac Glory' (unpatented), but with the distinctive and advantageous characteristics of year-around culture and larger flowers than 'Lilac Glory'.

I claim:

1. A new and distinctive alstroemeria cultivar, substantially as herein shown and described, characterized by its butterfly formation and abundant production of medium large flowers particularly distinguished by the reddish violet coloring of its relatively large outer petals, and its smaller and multi-colored inner petals which are heavily striped from base to tip.

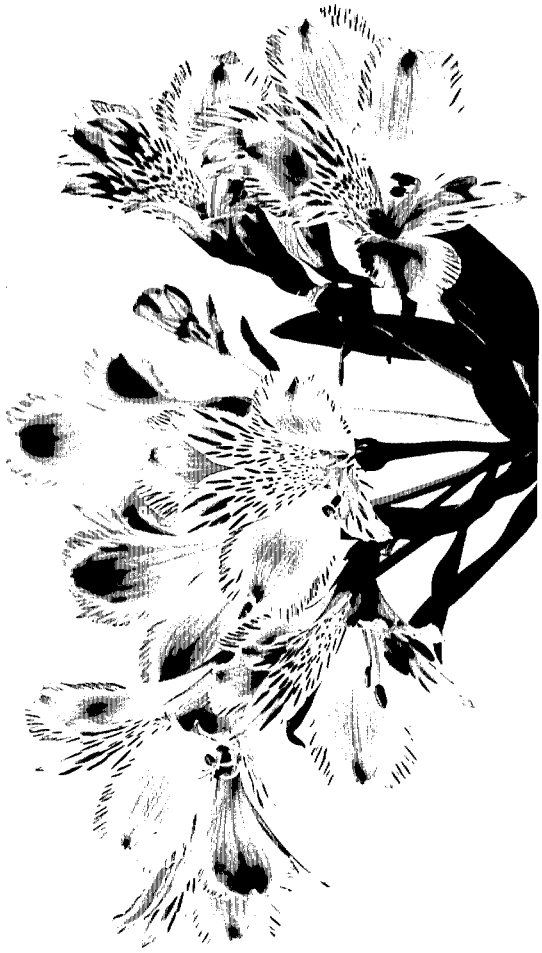
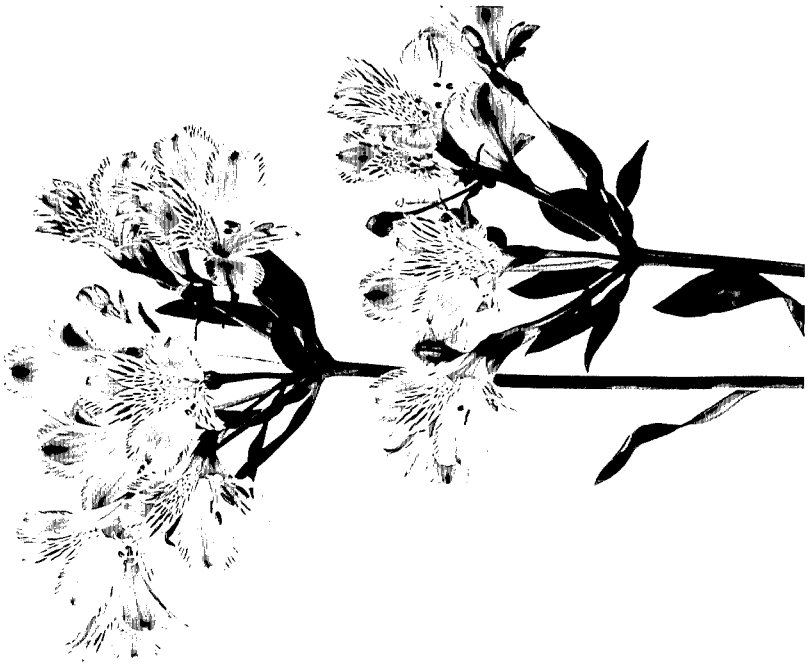

* * * * *